(12) United States Patent
Liu et al.

(10) Patent No.: US 9,884,009 B2
(45) Date of Patent: Feb. 6, 2018

(54) PLANT COMPOSITION HAVING MOISTURIZING, ANTI-WRINKLE, AND ANTI-ALLERGIC EFFICACIES, AND PREPARATION METHOD THEREOF

(71) Applicant: INFINITUS (CHINA) CO., LTD, Guangdong (CN)

(72) Inventors: Guangrong Liu, Guangdong (CN); Zidan Li, Guangdong (CN)

(73) Assignee: INFINITUS (CHINA) CO., LTD, Jiangmen (CN)

( * ) Notice: Subject to any disclaimer, the term of this patent is extended or adjusted under 35 U.S.C. 154(b) by 0 days.

(21) Appl. No.: 14/913,941

(22) PCT Filed: May 9, 2014

(86) PCT No.: PCT/CN2014/077149
§ 371 (c)(1),
(2) Date: Feb. 23, 2016

(87) PCT Pub. No.: WO2015/024396
PCT Pub. Date: Feb. 26, 2015

(65) Prior Publication Data
US 2016/0296461 A1    Oct. 13, 2016

(30) Foreign Application Priority Data
Aug. 23, 2013    (CN) .......................... 2013 1 0374302

(51) Int. Cl.
| | | |
|---|---|---|
| *A61K 8/97* | (2017.01) | |
| *A61K 36/07* | (2006.01) | |
| *A61K 36/8968* | (2006.01) | |
| *A61K 36/8984* | (2006.01) | |
| *A61K 36/86* | (2006.01) | |
| *A61Q 19/00* | (2006.01) | |
| *A61Q 19/08* | (2006.01) | |
| *A61K 36/899* | (2006.01) | |

(52) U.S. Cl.
CPC ................ *A61K 8/97* (2013.01); *A61K 36/07* (2013.01); *A61K 36/86* (2013.01); *A61K 36/899* (2013.01); *A61K 36/8968* (2013.01); *A61K 36/8984* (2013.01); *A61Q 19/007* (2013.01); *A61Q 19/08* (2013.01); *A61K 2236/331* (2013.01); *A61K 2236/37* (2013.01); *A61K 2236/53* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,716,605 A | * | 2/1998 | Onitsuka | ................ A61K 8/365 424/70.1 |
| 7,935,684 B2 | | 5/2011 | Wu | |
| 2006/0222608 A1 | * | 10/2006 | Yang | ........................ A61K 8/73 424/62 |
| 2011/0045105 A1 | * | 2/2011 | Paufique | .................. A61K 8/73 424/725 |

FOREIGN PATENT DOCUMENTS

| | | | | |
|---|---|---|---|---|
| CN | 102105155 | | 6/2011 | |
| CN | 102274138 | | 12/2011 | |
| CN | 102274138 A | * | 12/2011 | ............... A61K 8/97 |
| CN | 102370605 | | 3/2012 | |
| KR | 794518 B1 | * | 1/2008 | |

OTHER PUBLICATIONS

Chen Gang, Antioxidant Activity, Moisture-absorbing and Moisture-retention Properties of Polysaccharides from Tremella, Oat and Ophiopogon Japonicus,Chinese Archives of Traditional Chinese Medicine, Jan. 2013, pp. 212-214, vol. 31 No. 1, China Academic Journal Electronic Publishing House, Beijing China.

* cited by examiner

*Primary Examiner* — Bethany Barham
*Assistant Examiner* — Peter Anthopolos
(74) *Attorney, Agent, or Firm* — Kirton McConkie; Evan R. Witt

(57) ABSTRACT

Provided is a moisturizing, anti-wrinkle, and anti-allergic traditional Chinese medicine composition and a preparation method thereof. The traditional Chinese medicine composition has an aqueous extract of *Dendrobium nobile, Viola tricolor, Ophiopogon japonicus, Tremella fuciformis*, and an oat material as active ingredient. The oat material is oat grains, oat flour, or oat bran. In the composition, the *Dendrobium nobile, Viola tricolor, Ophiopogon japonicus, Tremella fuciformis* and oat material have a weight ratio of 5-15:2-10:2-10:1-5:1-5, and preferably 12:6:3:2:2. The *Dendrobium nobile, Viola tricolor, Ophiopogon japonicus*, oat material, and *Tremella fuciformis* are combined and extracted for external use, with which moisturizing and also delaying skin aging, anti-allergic and anti-chapping efficacies are achieved by means of water retention, maintenance of normal physiological functions of aquaporins, and others.

10 Claims, 2 Drawing Sheets

PLANT COMPOSITION HAVING MOISTURIZING, ANTI-WRINKLE, AND ANTI-ALLERGIC EFFICACIES, AND PREPARATION METHOD THEREOF

FIELD OF THE INVENTION

The present invention relates to the field of technical development of cosmetics, and more particularly to a plant composition having moisturizing, anti-wrinkle, and anti-allergic efficacies, and a preparation method thereof.

BACKGROUND OF THE INVENTION

Modern people suffer from skin itching, wrinkling, allergy, and other dry skin related problems. The skin has an adequate moisture content, which lays the basis for skin barrier, absorption, metabolism, and other physiological functions. Adequate hydration is favorable to enzymatic reaction, and can facilitate the maturization of the stratum corneum and allow the stratum corneum to remain elastic. Adequate hydration is also favorable to the expansion, and reduction in structural compactness, of the cells in the stratum corneum, such that the permeability is increased. Regular reflection from a stratum corneum layer with a high moisture content gives rise to a bright glow. In contrast, the light is non specularly reflected from a dry and squamous stratum corneum layer, such that the skin looks dim. Therefore for a majority of women, the skin protection is currently focused on moisturizing of the skin, and thus the moisturizing efficacy has become a critical aspect of the skin care products.

The moisture retention ability of the skin mainly depends on the stratum corneum, since the stratum corneum functions as a barrier against water loss. The stratum corneum comprises water soluble moisturizing substances such as amino acids or salts thereof, carbohydrates, and so on (referred to as natural moisturizing factors, NMFs), and oil ingredients such as cellular lipids and sebum (those present in epidermis are referred to as epidermal sebum), in which the natural moisturizing factors account for 30% and the oil ingredients account for 11%. The oil ingredients are in association with, or encircle the natural moisturizing factors, to prevent them from outflow, thus playing a role in controlling the moisture volatilization. In addition, several aquaporins exist in the skin, which affect the transport of water in the skin. Aquaporin 3 (AQP3) is the mostly expressed aquaporin in the skin, which is rather abundant in human epidermal keratinocytes and stratum corneum as detected by RT-PCR. AQP3 is of great importance for water retention in keratinocytes. It is found through observations on the phenotype of AQP3 gene knockout nude mice that the mice are substantially normally developed, except that the moisture content in the epidermal keratinocytes in the AQP3 gene knockout nude mice is considerably reduced, and the water loss is obviously higher than that in normal mice, when exposed to dry conditions.

"Healthy and natural" is the development philosophy of the cosmetic industry. China is long in history of manufacturing and using natural plant cosmetics and rich in practical experiences, and has a technical superiority. Moreover, China has vast territory and rich natural resources, where various distinctive plants are grown due to its unique geographical environment and climatic conditions. Because of their different characteristics, these plants have long been used in cosmetology, and have the effect of nourishing the skin and protecting the skin against the adverse effects from external harmful agents.

In view of this, a cosmetic additive is developed from natural plants in this patent, which is mainly characterized by moisturizing efficacy and also by anti-aging and anti-allergic efficacies. The extracts from many plants are combined, which synergize by means of film forming, water retention, maintenance of normal physiological functions of aquaporins, and others to exert comprehensive moisturizing, anti-wrinkle, and anti-allergic effects.

SUMMARY OF THE INVENTION

An objective of the present invention is to provide a plant composition having moisturizing, anti-wrinkle, and anti-allergic efficacies, and a preparation method thereof.

The traditional Chinese medicine composition provided in the present invention has, as active ingredient, an aqueous extract from the raw material mixture of:

*Dendrobium nobile, Viola tricolor, Ophiopogon japonicus, Tremella fuciformis*, and an oat material;

where the oat material is oat grains, oat flour, or oat bran.

In the composition, the oat grains may have or have no bran.

The oat flour is a whole oat flour or a refined oat flour, where the whole oat flour is obtained by pulverizing the whole oat grains and sieving through a screen of 100 meshes.

The *Dendrobium nobile, Viola tricolor, Ophiopogon japonicus, Tremella fuciformis*, and oat material have a weight ratio of 5-15:2-10:2-10:1-5:1-5, and specifically 12:6:3:2:2, 5:8:2:1:1, 12:3:6:5:4, 5-12:3-8:1-5:1-4, or 12:3-6:2-5:2-4.

For the aqueous extract, the weight ratio of water to *Dendrobium nobile* used in the water extraction step is 160-220:5-15, and specifically 160:12, 220:5, 200:12, 160-200:12, 200-220:5-12, or 160-220:5-12.

The aqueous extract is prepared through a process comprising:

uniformly mixing the *Dendrobium nobile, Viola tricolor, Ophiopogn japonicus, Tremella fuciformis*, oat material and water in proportion and extracting.

In the extraction step, the temperature is 60-100° C., and specifically 65, 80, 100, 65-100, 80-100, or 65-80° C.; and the time is 1-4 hrs, and specifically 2 hrs.

The method for preparing the composition provided in the present invention comprises:

uniformly mixing the *Dendrobium nobile, Viola tricolor, Ophiopogon japonicus, Tremella fuciformis*, oat material, and water at a ratio as defined in claim 2 or 3, and extracting, to obtain an aqueous extract.

In the extraction step of the method, the temperature is 60-100° C., and specifically 80° C.; and the time is 1-4 hrs, and specifically 1, 2, 4, 1-2, or 2-4 hrs.

The method further comprises:

after the extraction step, standing and then filtering the resultant aqueous extract, and collecting the filtrate.

In the standing step, the temperature is room temperature and the time is 1-4 hrs, and specifically 1, 2, or 4 hrs.

In the filtering step, the filter has a hole number of 100-200 meshes.

Additionally, use of the composition according to the present invention in the preparation of products having any one of the functions below is also contemplated in the protection scope of the present invention:

1) moisturizing;
2) anti-aging;
3) anti-allergy; and
4) anti-chapping.

In the present invention, the *Dendrobium nobile, Viola tricolor, Ophiopogon japonicus*, oat material, and *Tremella fuciformis* are combined and extracted for external use, with which moisturizing and also delaying skin aging, anti-allergic and anti-chapping efficacies are achieved by means of water retention, maintenance of normal physiological functions of aquaporins, and others.

DETAILED DESCRIPTION OF THE INVENTION

Figure 1:
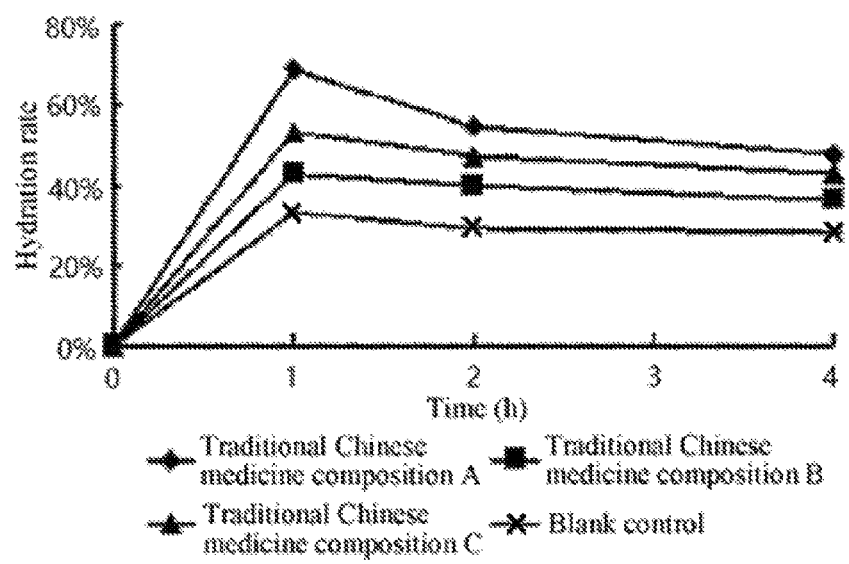
FIG. 1 is a plot showing changes in percent water content on skin's surface vs time.

Hereinafter, the present invention is further elucidated with reference to specific examples. However, the present invention is not limited thereto. The methods are all conventional methods, unless it is otherwise stated. The raw materials are all publicly commercially available unless it is otherwise stated.

Example 1

A traditional Chinese medicine composition was prepared following the steps below.

1) *Dendrobium nobile, Ophiopogon japonicus*, and *Tremella fuciformis* were chopped, and *Viola tricolor* and oat bran were pulverized. Then, the *Dendrobium nobile, Ophiopogon japonicus, Tremella fuciformis, Viola tricolor*, oat bran, and water were uniformly mixed at a weight ratio of *Dendrobium nobile:Viola tricolor:Ophiopogon japonicus:Tremella fuciformis*:oat bran:water=12:6:3:2:2:160, transferred to an electric-heated thermostatic water bath, and extracted at 80° C. for 2 hrs. The solution obtained after extraction was removed from the thermostatic water bath, allowed to stand at room temperature and cool for 2 hrs to normal temperature, and then roughly filtered with gauze of 200 meshes. A filtrate was obtained after the dregs were filtered off. Two layers of filter paper were laid in a Buchner filter, and a layer of diatomaceous earth that was about 0.5 cm thick was sandwiched between the filter paper. The filtrate obtained after rough filtration was suction filtered under vacuum, and the filtrate was collected, to obtain a traditional Chinese medicine composition A of the present invention.

Example 2

A traditional Chinese medicine composition was prepared following the steps below.

1) *Dendrobium nobile, Ophiopogon japonicus*, and *Tremella fuciformis* were chopped, and *Viola tricolor* and oat bran were pulverized. Then, the *Dendrobium nobile, Ophiopogon japonicus, Tremella fuciformis, Viola tricolor*, oat bran, and water were uniformly mixed at a weight ratio of *Dendrobium nobile:Viola tricolor:Ophiopogon japonicus: Tremella fuciformis*:oat bran:water=5:8:2:1:1:220, transferred to an electric-heated thermostatic water bath, and extracted at 100° C. for 4 hrs. The solution obtained after extraction was removed from the thermostatic water bath, allowed to stand at room temperature and cool for 4 hrs to normal temperature, and then roughly filtered with gauze of 100 meshes. A filtrate was obtained after the dregs were filtered off. Two layers of filter paper were laid in a Buchner filter, and a layer of diatomaceous earth that was about 0.5 cm thick was sandwiched between the filter paper. The filtrate obtained after rough filtration was suction filtered under vacuum, and the filtrate was collected, to obtain a traditional Chinese medicine composition B of the present invention.

Example 3

A traditional Chinese medicine composition was prepared following the steps below.

1) *Dendrobium nobile, Ophiopogon japonicus*, and *Tremella fuciformis* were chopped, and *Viola tricolor* and oat bran were pulverized. Then, the *Dendrobium nobile, Ophiopogon japonicus, Tremella fuciformis, Viola tricolor*, oat bran, and water were uniformly mixed at a weight ratio of *Dendrobium nobile:Viola tricolor:Ophiopogon japonicus: Tremella fuciformis*:oat bran:water=12:3:6:5:4:200, transferred to an electric-heated thermostatic water bath, and extracted at 65° C. for 1 hr. The solution obtained after extraction was removed from the thermostatic water bath, allowed to stand at room temperature and cool for 1 hr to normal temperature, and then roughly filtered with gauze of 200 meshes. A filtrate was obtained after the dregs were filtered off. Two layers of filter paper were laid in a Buchner filter, and a layer of diatomaceous earth that was about 0.5 cm thick was sandwiched between the filter paper. The filtrate obtained after rough filtration was suction filtered under vacuum, and the filtrate was collected, to obtain a traditional Chinese medicine composition C of the present invention.

Example 4. Evaluation of the Moisturizing Effect of the Traditional Chinese Medicine Compositions A, B, and C Obtained in Examples 1, 2, and 3

1. Moisturizing Effect—Test of Hydration Rate in Stratum Corneum/Water Loss in Stratum Corneum of Human Skin The test sample was a cream, which was formulated following a process below.

Any one of the traditional Chinese medicine compositions obtained in Examples 1-3 was added to a phase B of a blank cream base, to obtain a cream, in which the content of the traditional Chinese medicine composition in the cream was 5% by weight.

The traditional Chinese medicine composition A obtained in Example 1 corresponded to the Cream 1, the traditional Chinese medicine composition B obtained in Example 2 corresponded to the Cream 2, and the traditional Chinese medicine composition C obtained in Example 3 corresponded to the Cream 3.

Additionally, the blank cream base was used as a blank control.

The blank cream base was prepared as follows.

According to the formulation in Table 1, the raw materials in the phase A were uniformly mixed and heated to 82° C.; the raw materials in the phase B were uniformly mixed and heated to 82° C.; and the phase A was slowly added to the phase B while the phase B was homogenized at 2000 r/min, and then homogenized for 5 min. After homogenization, the system was stirred and cooled, and the phase C was added when the temperature reached to 40° C., and stirred until uniform, to obtain the blank cream base.

The result shows that the traditional Chinese medicine compositions obtained in the examples all have good anti-drying moisturizing effect, with the anti-drying moisturizing effect of the traditional Chinese medicine composition A obtained Example 1 being the highest.

TABLE 1

Formulation of the blank cream base

| Phase | Raw material | INCI name | Amount (wt %) | Supplier |
|---|---|---|---|---|
| A | EC.FIX.SE | Sucrose stearate/cetearyl glucoside/cetyl alcohol | 2.00 | Nuoxin Fine Chemical Research Institute |
|  | Alcohol mixture | Cetostearyl alcohol | 1.50 | Cognis Chemicals Co., Ltd |
|  | Monoglyceride | Glyceryl stearate | 1.00 | Danisk (China) Co., Ltd |
|  | White oil | Paraffinum liquidum | 1.00 | Connell Bros. (Shanghai) Co., Ltd. |
|  | IPM | Isopropyl myristate | 3.00 | Croda International Public Limited Company, UK |
|  | DM100 | Dimethicone | 3.00 | Wacker Chemical Bros. (Shanghai) Co., Ltd. |
| B | Water |  | To 100 |  |
|  | Glycerol | Glycerol | 4.00 | P & G Chemicals |
|  | Butanediol | Butanediol | 3.00 | Oxea Corporation, US |
|  | Xanthan gum | Xanthan gum | 0.10 | CP Kelco Us, Inc. |
|  | EDTA-2Na | Disodium EDTA | 0.03 | AkzoNobel |
| C | MTI | Methyl isothiazolinone/Iodopropynyl butylcarbamate | 0.15 | Thor Corporation, UK |

Before test, 30 healthy subjects (male:female 15:15) of 20-30 years old were enrolled who have received professional training, and had no history of skin or systemic diseases. There was no abnormality in the test sites, and no agents or cosmetics irrelevant to the experiment were applied during test.

The test location was set at room temperature (25±1)° C., and set to have a relative humidity of (40±5)%. The subjects were maintained in homeostasis before test. The test began after the subjects had their two arms cleaned with water at about 35° C., and then sit quietly for 30 min in the test environment.

A test area (4 cm×4 cm) was marked at an inner flank of the arm of the test subjects that was 5 cm to the basal portion of the hand, and multiple areas (at an interval of 1 cm) may be marked at the same arm. The test samples were distributed at random. A blank value was measured from each test area initially. Then, the test sample was singly applied at a dosage of (2.0±0.1) mg/cm$^2$. The water hydration rate and the water loss in the skin of the test and blank control areas were measured by using a multi-functional skin water content tester and a transepidermal water loss tester at 0.5 hr, 1 hr, 2 hrs and 4 hrs after application respectively.

During test, 5 measurements obtained from an area of the subject that was applied with the same sample were averaged, and analyzed by t-test using SPSS.

Experimental Results (1) Change in Skin Water Content

The change in water content reflects the change rule of water content in the experimental area over time during the test period. The higher the value is, the higher the water content is. Or otherwise, the lower the value is, the lower the water content is.

Hydration rate=(Water content of the sample group−Initial water content)/Initial water content The result is as shown in FIG. 1.

(2) Change in Transepidermal Water Loss

Transepidermal water loss (TEWL) reflects the change rule of water loss in the experimental area over time during the test period, by which the water holding capacity of the test sample may be characterized. The lower the value is, the smaller the water loss is, and the higher the water holding capacity is. Or otherwise, the higher the value is, the lower the water holding capacity is.

Water loss (%)=(Water loss of the sample group−Initial water loss)/Initial water loss×100

Figure 2:
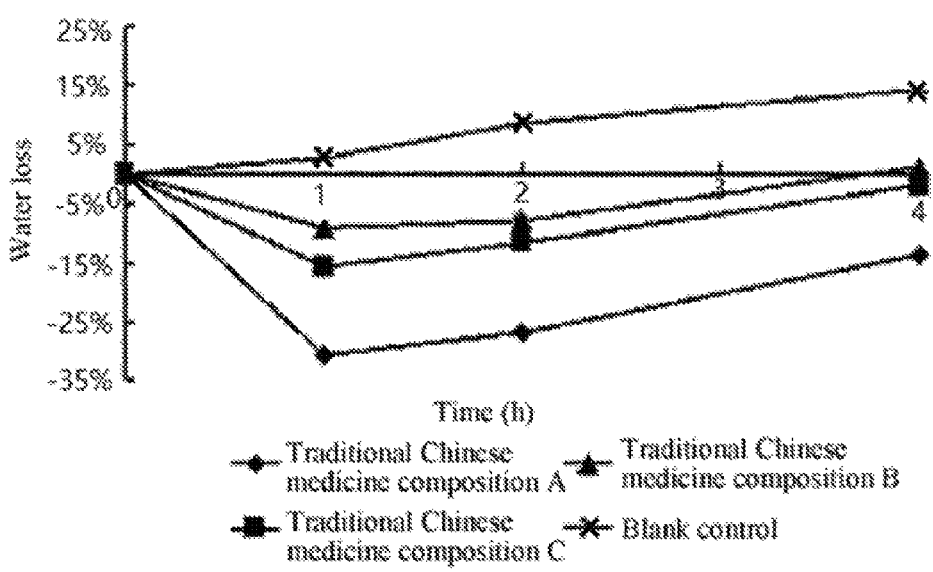
FIG. 2 is a plot showing changes in water loss on skin's surface vs time.

The water loss result is as shown in FIG. 2.

The result shows that within 4 hrs, the traditional Chinese medicine compositions obtained in the examples all have water holding capacity, and the traditional Chinese medicine composition A has the lowest water loss and thus the most prominent water holding capacity.

In summary, the traditional Chinese medicine composition provided in the present invention allows the skin water content to increase and the water loss to decrease, thus having a good water holding capacity and an obvious moisturizing effect on the skin.

Example 5. Effect of the Traditional Chinese Medicine Compositions a, B, and C Obtained in Examples 1, 2, and 3 on the mRNA Expression Level of AQP3

Aquaporins (AQPs) are a class of membrane transporter proteins correlating with the transmembrane transport of water, glycerol and some small molecular substances. AQP3 is expressed in various tissues and organs including skin. The normal epidermal KC expresses AQP3 only in the basal cell layer. The AQP3 provides a channel for the membrane of the epithelial cells, to maintain the intracellular osmotic pressure and cell volume, and plays a role in the transport of water. The glycerol transport function of AQP3 plays a critical role in hydration, elasticity maintenance and repair post damage of the skin. The composition in this invention can repair the skin barrier and improve the water content in the stratum corneum by means of moisturizing and also potential regulation of the AQP3 level. After the traditional Chinese medicine compositions A, B, and C as solutions were applied to C3H mice, the mRNA expression level of AQP3 in the skin of the mice was detected by real-time quantitative PCR, in which saline was used as a control.

Experimental Method:

(1) Grouping: 20 test mice were assigned to a Sample Group A with the composition of Example 1, a Sample Group B with the composition of Example 2, a Sample Group C with the composition of Example 3, and a negative control group, each group having 5 animals.

Sample group: The traditional Chinese medicine composition obtained in any one of Examples 1-3 was uniformly mixed with deionized water at a weight ratio of 5:95, to obtain a solution of the traditional Chinese medicine composition in water, which was applied onto the experimental mice once a day.

Control group: The animals in this group were applied with saline once a day, that is, the skin was kept in normal physiological state.

(2) The mice were removed of the hair from the upper abdomen by using a depilatory cream, applied with the compositions respectively in accordance with their groups once a day, and housed in a box after absorption. The mice were sacrificed after 30 days, and the skin was removed.

(3) The epidermis was isolated from the skin by using a dispase, and dissociated into individual keratinocytes by using a pancreatin. The RNA in the keratinocytes was extracted with Trizol, reversely transcribed into cDNA, and then detected by real-time quantitative PCR (SYBR GREEN) (QIAGEN 204143). The PCR primer sequence and conditions were as follows: aqp3 sense: 5'-TTGGTG-GCTGGCCAAGTGTC-3' (SEQ ID NO. 1); aqp3 antisense: 5'-GTCTGTGCCAGTGCATAGAT-3' (SEQ ID NO. 2); B-actin sense: 5'-TGTATGCCTCTGGTCGTACC-3' (SEQ ID NO. 3); B-actin antisense: 5'-CAGGTCCAGACGCAG-GATG-3' (SEQ ID NO. 4).

35 cycles of 94° C. for 2 min; 94° C. for 40 s; 62° C. for 30 s; and 72° C. for 20 s.

(4) Statistical analysis method: The results were analyzed by One-way ANOVA and t test.

The mRNA expression levels of AQP3 following processing with different methods are shown in Table 2.

TABLE 2

Effect of different amounts of compositions as solution on AQP3 expression level in mouse skin

| Group | AQP3/B-actin |
|---|---|
| Sample Group A with the composition of Example 1 | (5.004 ± 0.015)E−03* |
| Sample Group B with the composition of Example 2 | (4.08 ± 0.05)E−03 |
| Sample Group C with the composition of Example 3 | (4.31 ± 0.17)E−03 |
| Negative control group | (3.89 ± 0.26)E−03 |

*denotes $P < 0.05$, compared with the blank control

The experimental results show that the traditional Chinese medicine composition up-regulates the mRNA expression level of AQP3 in normal mouse skin, and enhances the skin hydration by promoting the transport of water or glycerol in the stratum corneum. The production of water-binding molecules (e.g. hyaluronic acid) in the skin is increased, and thus the skin dryness and peeling phenomena are alleviated.

Example 6. Evaluation of the Anti-Aging Effect of the Traditional Chinese Medicine Compositions A, B, and C Obtained in Examples 1, 2, and 3

Modern researches suggest that skin photoaging may be caused by sunlight irradiation. UV (in the sunlight) irradiation can cause oxidative stress and production of excessive free radicals in the skin, thus leading to cell damage. Meanwhile, IR irradiation can cause the high expression of matrix metalloproteinase-1 (MMP-1) in dermal cells of the skin, whereby the degradation of elastin and collagen in the dermis is accelerated, thus leading to lost elasticity and deepened wrinkle of the skin. The traditional Chinese medicine composition provided in this patent has the free radical-scavenging and MMP-1 inhibiting efficacies, and can slow down the skin photoaging caused by UV and IR irradiation.

1) Free Radical-Scavenging Efficacy

DPPH, chemical name 1,1-diphenyl-2-picryl-hydrazyl, is a stable organic free radical. The free radical-scavenging efficacy of the traditional Chinese medicine compositions A, B, and C obtained in Examples 1, 2, and 3 was quantitatively analyzed by spectrophotometry.

The traditional Chinese medicine composition obtained in any one of Examples 1-3 was uniformly mixed with deionized water at a weight ratio of 5:95, to obtain a solution of the traditional Chinese medicine composition in water.

The solution of the traditional Chinese medicine composition in water was used in test.

The traditional Chinese medicine composition A obtained in Example 1 corresponded to a Sample 1;

The traditional Chinese medicine composition B obtained in Example 2 corresponded to a Sample 2; and The traditional Chinese medicine composition C obtained in Example 3 corresponded to a Sample 3.

An aqueous solution of a vitamin C derivative was used as a positive control in the test in place of the traditional Chinese medicine composition.

Figure 3:
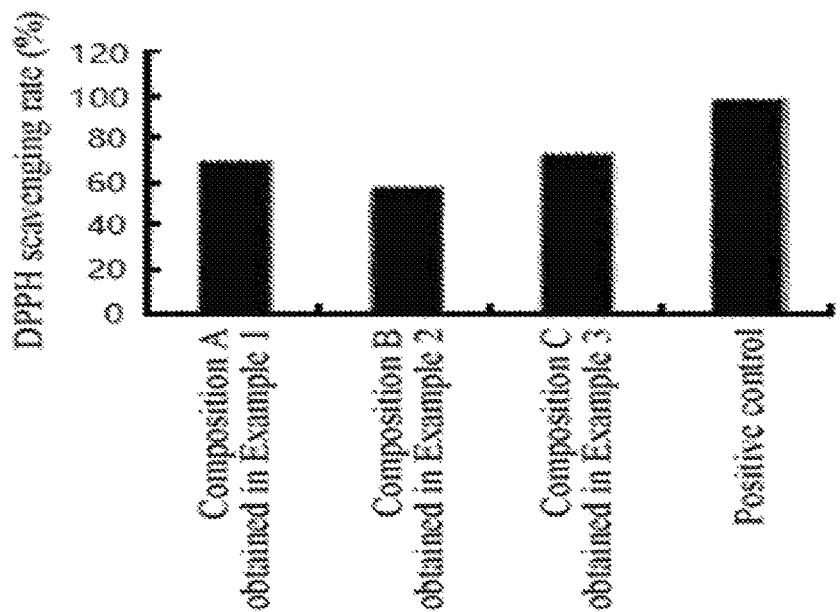
FIG. 3 shows clearance of DPPH by the composition.

The determination results are shown in FIG. 3.

The experimental results show that when present in an aqueous solution in a content of 5.0% by weight, the traditional Chinese medicine compositions obtained in the examples all have DPPH scavenging ability and can reduce the effective concentration of hydroxyl radicals, alkyl radicals or oxygen radicals and disrupt the lipid peroxidation, thus having a good effect on delaying the skin photoaging.

2) Inhibition on Matrix Metalloproteinase-1

The effect of the traditional Chinese medicine compositions on MMP-1 activity was detected by fluorogenic substrate assay. The experimental method was as described in *Establishment and application of two in Vitro screening methods for cosmetic additives with anti-aging effect* (Lai Jixiang, 2007).

The traditional Chinese medicine composition obtained in any one of Examples 1-3 was uniformly mixed with deionized water at a weight ratio of 5:95, to obtain a solution of the traditional Chinese medicine composition in water.

The above aqueous solutions were assayed. The results are shown in Table 3.

TABLE 3

Inhibition of the composition on MMP-1

| No. | Name | Inhibition (%) |
|---|---|---|
| 1 | Composition A obtained in Example 1 | 81.63 |
| 2 | Composition B obtained in Example 2 | 47.64 |
| 3 | Composition C obtained in Example 3 | 60.98 |

The results show that the compositions obtained in the examples all have inhibition on MMP-1 produced due to induction with IR irradiation, and can reduce the over-degradation of elastin and collagen caused by sunlight irradiation, thereby keeping the skin elastic and alleviating the skin photoaging.

Example 7. Evaluation of the Anti-Allergic Effect of the Traditional Chinese Medicine Compositions A, B, and C Obtained in Examples 1, 2, and 3

Hyaluronic acid is an ingredient present in tissue matrices that limits the dispersion of water and other extracellular materials. After hydrolysis catalyzed by hyaluronidase, the cells become non-viscous therebetween, cell degranulation occurs and the newly synthesized media are leaked, such that a biological effect is exerted, and fast onset of allergic reaction is caused. Therefore, the remission and amelioration of type I hypersensitivity by a sample is generally indicated by the inhibition of the sample on hyaluronidase.

The inhibition of the traditional Chinese medicine compositions A, B, and C obtained in Examples 1, 2, and 3 on hyaluronidase was determined following a process below.

The traditional Chinese medicine composition A obtained in Example 1 was uniformly mixed with deionized water at a weight ratio of 5:95, to obtain a sample solution C1.

The traditional Chinese medicine composition B obtained in Example 2 was uniformly mixed with deionized water at a weight ratio of 5:95, to obtain a sample solution C2.

The traditional Chinese medicine composition C obtained in Example 3 was uniformly mixed with deionized water at a weight ratio of 5:95, to obtain a sample solution C3.

The test was triplicated.

Each replication was set as follows.

7 test tubes were designated as A, B, C1-C3, D, and E.

The reagents were added in sequence as shown in respective columns in Table 4, and amenable to operations in corresponding steps.

The tube A was added with a control solution and corresponded to the column A in Table 4.

The tube B was added with a blank control solution and corresponded to the column B in Table 4.

The tube D was added with a sample blank solution and corresponded to the column D in Table 4.

The tube E was added with a positive control solution and corresponded to the column E in Table 4.

The tubes C1-C3 were all added with reagents in sequence as shown in column C in Table 4.

The sample solution added to the tube C1 was the sample solution C1.

The sample solution added to the tube C2 was the sample solution C2.

The sample solution added to the tube C3 was the sample solution C3.

The absorbance, that is, ABS value, of respective tubes at 555 nm was measured, and then the inhibition of the sample solution on hyaluronidase was calculated according to a formula below for calculating the anti-allergic activity:

Inhibition of the sample on hyaluronidase=[(A-B)−(C-D)]/(A-B)×100%

Inhibition of the positive control on hyaluronidase=[(A-B)−(E-D)]/(A-B)×100%

In the two formulas, A is the ABS value of the tube A;
B is the ABS value of the tube B;
C is the ABS value of the tube C;
D is the ABS value of the tube D; and
E is the ABS value of the tube E.

The ABS value of the tube C was determined as follows.

1) 0.1 mL of a 0.25 mmol/L $CaCl_2$ solution and 0.5 mL of a hyaluronidase solution were incubated for 20 min in a water bath at 37° C.

2) 0.5 mL of the treated sample solution was added, and continuously incubated for 20 min in a water bath at 37° C.

3) 0.5 mL of an aqueous sodium hyaluronate solution was added, incubated for 20 min in a water bath at 37° C., and then stood at normal temperature for 5 min.

4) 0.1 mL of 0.4 mol/L aqueous NaOH solution and 0.5 mL acetylacetone were then added, heated for 15 min in a boiling water bath, and then cooled for 5 min immediately with ice water.

5) 1.0 mL Ehrlich reagent was added, diluted with 3.0 mL absolute ethanol, and developed by standing at normal temperature for 20 min. The absorbance was determined by using a spectrophotometer, to obtain the ABS value of the tube C containing the sample solution.

The experimental steps of Groups A to E are also shown in Table 4.

TABLE 4

Operations in experiment for testing inhibition on hyaluronidase

| Experimental steps | Reagent | Group A | Group B | C | Group D | Group E |
|---|---|---|---|---|---|---|
| 1) 20 min in a water bath at 37° C. | 0.1 ml $CaCl_2$ solution | + | + | + | + | + |
| | 0.5 ml hyaluronidase solution | + | − | + | − | + |
| 2) 20 min in a water bath at 37° C. | 0.5 ml sample solution | − | − | + | + | − |
| 3) 30 min in a water bath at 37° C. stand at normal temperature for 5 min | 0.5 ml sodium hyaluronate solution | + | + | + | + | + |
| 4) heated in boiling water for 15 min, and then cooled with ice water for 5 min | 0.1 ml NaOH solution | + | + | + | + | + |
| | 0.5 ml acetylacetone | + | + | + | + | + |

TABLE 4-continued

Operations in experiment for testing inhibition on hyaluronidase

| Experimental steps | Reagent | Group A | Group B | C | Group D | Group E |
|---|---|---|---|---|---|---|
| 5) stand at normal temperature for 20 min | 1.0 ml Ehrlich reagent | + | + | + | + | + |
| | 3.0 ml absolute ethanol | + | + | + | + | + |
| | measured at absorption maximum wavelength | | | | | |

Note:
"+" denotes that this item is added, and "−" denotes that this item is not added, but replaced by equal volume of acetate buffer solution. "*" denotes that this item is replaced by equal volume of 5% by weight of aqueous dipotassium glycyrrhizinate solution.

Figure 4:
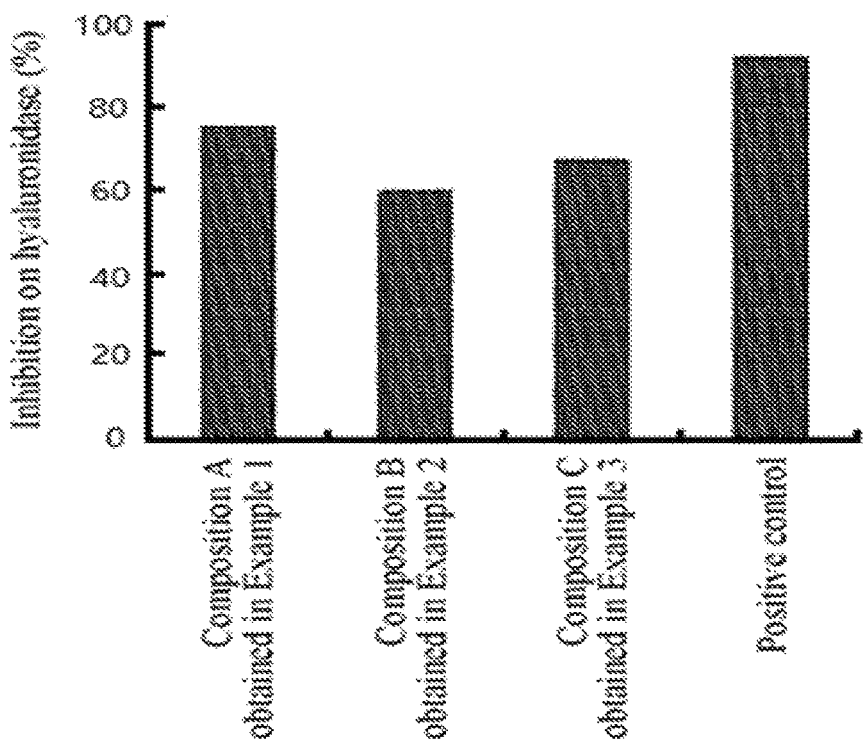
FIG. 4 shows inhibition of the composition on hyaluronidase.

The result is as shown in FIG. 4.

The inhibition of the composition A obtained in Example 1 on hyaluronidase is 75.32%.

The inhibition of the composition B obtained in Example 2 on hyaluronidase is 59.89%.

The inhibition of the composition C obtained in Example 3 on hyaluronidase is 67.26%.

The inhibition of the tube E, that is, the positive control, on hyaluronidase is 92.12%.

The experimental results show that the compositions obtained in the examples all have in-vitro hyaluronidase inhibiting efficacies, and can inhibit the release of allergic mediators, thus having a good anti-allergic effect.

Example 8. Evaluation of the Anti-Chapping Effect of the Traditional Chinese Medicine Compositions A, B, and C Obtained in Examples 1, 2, and 3

3% of the traditional Chinese medicine composition A was added to a phase B of a blank cream base formulation as shown in Table 5, and uniformly mixed, to obtain a cream containing the composition of Example 1.

A cream containing the composition of Example 2 and a cream containing the composition of Example 3 were obtained following a process the same as above, except that the traditional Chinese medicine composition A was replaced by the traditional Chinese medicine composition B obtained in Example 2 or the traditional Chinese medicine composition C obtained in Example 3.

The above three creams were used in human foot skin application test for a period of 1 month (in winter). 120 subjects were enrolled, and assigned to 4 groups at random, that is, a Group A, a Group B, a group C, and a blank control group (blank cream base), each group having 30 subjects.

The group A was applied with the cream containing the composition of Example 1.

The group B was applied with the cream containing the composition of Example 2.

The group C was applied with the cream containing the composition of Example 3.

The blank cream base was prepared as follows.

According to the formulation in Table 5, the raw materials in the phase A were uniformly mixed and heated to 82° C.; the raw materials in the phase B were uniformly mixed and heated to 82° C.; and the phase A was slowly added to the phase B while the phase B was homogenized at 2000 r/min, and then homogenized for 5 min. After homogenization, the system was stirred and cooled, and the phase C was added when the temperature reached to 40° C., and stirred until uniform, to obtain the blank cream base.

TABLE 5

Formulation of blank cream base

| Phase | Raw material | INCI name | Amount (wt %) | Supplier |
|---|---|---|---|---|
| A | EC.FIX.SE | Sucrose stearate/cetearyl glucoside/cetyl alcohol | 2.00 | Nuoxin Fine Chemical Research Institute |
| | Alcohol mixture | Cetostearyl alcohol | 1.50 | Cognis |
| | Monoglyceride | Glyceryl stearate | 1.00 | Danisk |
| | White oil | Paraffinum liquidum | 1.00 | Connell |
| | IPM | Isopropyl myristate | 3.00 | Croda |
| | DM100 | Dimethicone | 3.00 | Wacker Chemical |
| B | Water | | To 100 | |
| | Glycerol | Glycerol | 4.00 | P & G Chemicals |
| | Butanediol | Butanediol | 3.00 | OXEA |
| | Xanthan gum | Xanthan gum | 0.10 | CP Kelco |
| | EDTA-2Na | Disodium EDTA | 0.03 | Akzo |
| C | MTI | Methyl isothiazolinone/Iodopropynyl butylcarbamate | 0.15 | Thor Corporation, UK |

After application, the users reflect that the product has both a nourishing effect, and a good healing and repair effect on the chapped would on the skin. The test results are shown in Table 6.

TABLE 6

Evaluation of the anti-chapping effect of the traditional Chinese medicine composition when applied to human

|  | Roughness improvement | | | Wettedness | | | Softness | | |
| --- | --- | --- | --- | --- | --- | --- | --- | --- | --- |
|  | Obvious | Ordinary | No | Obvious | Ordinary | No | Obvious | Ordinary | No |
| Composition A obtained in Example 1 | 21 | 7 | 2 | 23 | 7 | 0 | 22 | 7 | 1 |
| Composition B obtained in Example 2 | 15 | 12 | 3 | 25 | 5 | 0 | 18 | 10 | 2 |
| Composition C obtained in Example 3 | 17 | 11 | 2 | 25 | 5 | 0 | 20 | 10 | 0 |
| Blank control | 11 | 15 | 4 | 20 | 9 | 1 | 17 | 7 | 6 |

The investigation results confirm that the traditional Chinese medicine composition has the following characteristics.

1. The active ingredients of the traditional Chinese herbal medicine contained in the product can enhance the self protection ability of the skin, and stimulate the growth of the granulation tissue.

2. A protective film may be locally formed, to shorten the clotting time and reduce bleeding, which is conducive to wound healing.

3. The moisture in the skin may be effectively protected against loss without the greasy feeling of glycerol containing skin care products, such that the people feel soft and comfortable after use.

The active ingredients of the traditional Chinese herbal medicine contained in the product can enhance the self protection ability of the skin, and locally form a protective film to reduce bleeding, which is conducive to wound healing, and the user satisfaction is high.

What is claimed is:

1. A traditional Chinese medicine composition, comprising an aqueous extract from the raw material mixture of:
   Dendrobium nobile, Viola tricolor, Ophiopogon japonicus, Tremella fuciformis, and an oat material; and the Dendrobium nobile, Viola tricolor, Ophiopogon japonicus, Tremella fuciformis and oat material have a weight ratio of 5-15:2-10:2-10:1-5:1-5;
   wherein the oat material is oat grains, oat flour, or oat bran.

2. The composition according to claim 1, wherein for the aqueous extract, a weight ratio of water to Dendrobium nobile used in a water extraction step is 160-220:5-15.

3. The composition according to claim 2, wherein the aqueous extract is prepared through a process comprising:
   uniformly mixing the Dendrobium nobile, Viola tricolor, Ophiopogon japonicus, Tremella fuciformis, oat material and water and extracting;
   wherein in the extraction step, the temperature is 60-100° C. and the time is 1-4 hrs.

4. A method for preparing the composition according to claim 1, comprising:
   uniformly mixing Dendrobium nobile, Viola tricolor, Ophiopogon japonicus, Tremella fuciformis, oat material, and water in proportion as the Dendrobium nobile, Viola tricolor, Ophiopogon japonicus, Tremella fuciformis, oat material, and water have a weight ratio of 5-15:2-10:2-10:1-5:1-5:160-220; and
   extracting the uniform mixture, to obtain an aqueous extract.

5. The method according to claim 4, wherein in the extraction step, the temperature is 60-100° C. and the time is 1-4 hrs.

6. The method according to claim 4, further comprising:
   after the extraction step, standing the aqueous extract;
   filtering the aqueous extract with a filter;
   collecting the filtrate.

7. The method according to claim 6, wherein in the standing step, the temperature is room temperature and the time is 1-4 hrs; and in the filtering step, the filter has a mesh size of 100-200.

8. A product comprising the traditional Chinese medicine composition according to claim 1, wherein the product is formulated as:
   1) a moisturizing product;
   2) an anti-aging product;
   3) an anti-allergy product; or
   4) an anti-chapping product.

9. A product comprising the traditional Chinese medicine composition according to claim 2, wherein the product is formulated as:
   1) a moisturizing product;
   2) an anti-aging product;
   3) an anti-allergy product; or
   4) an anti-chapping product.

10. A product comprising the traditional Chinese medicine composition according to claim 3, wherein the product is formulated as:
    1) a moisturizing product;
    2) an anti-aging product;
    3) an anti-allergy product; or
    4) an anti-chapping product.

* * * * *

```
                         SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
ttggtggctg gccaagtgtc                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
gtctgtgcca gtgcatagat                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
tgtatgcctc tggtcgtacc                                              20

<210> SEQ ID NO 4
<211> LENGTH: 19
<212> TYPE: DNA
<213> ORGANISM: Artificial sequence
<220> FEATURE:
```

| | | |
|---|---|---|
| <223> OTHER INFORMATION: Synthetic primer | | |
| <400> SEQUENCE: 4 | | |
| caggtccaga cgcaggatg | | 19 |